United States Patent [19]

Andrews

[11] Patent Number: 5,121,747
[45] Date of Patent: Jun. 16, 1992

[54] HYBRID ORTHOSIS

[75] Inventor: Brian Andrews, Glasgow, Scotland

[73] Assignee: University of Strathclyde, Glasgow, Scotland

[21] Appl. No.: 233,928

[22] Filed: Aug. 11, 1988

Related U.S. Application Data

[63] Continuation of Ser. No. 928,061, Nov. 6, 1986, abandoned.

[30] Foreign Application Priority Data

Nov. 6, 1985 [GB] United Kingdom .................. 8527342
Jun. 23, 1986 [GB] United Kingdom .................. 8615269

[51] Int. Cl.⁵ ............................. A61N 1/32; A61F 5/00
[52] U.S. Cl. .................................. 128/423 W; 128/421; 602/2; 602/16; 602/23
[58] Field of Search ................... 128/421, 423, 423 W, 128/80 C, 80 F, 80 G, 68.1

[56] References Cited

U.S. PATENT DOCUMENTS

| | | | |
|---|---|---|---|
| 3,083,712 | 4/1963 | Keegan, Jr. ..................... | 128/423 W |
| 4,499,900 | 2/1985 | Petrofsky et al. ............. | 128/423 W |
| 4,558,704 | 12/1985 | Petrofsky ........................ | 128/423 R |
| 4,569,352 | 2/1986 | Petrofsky et al. ............. | 128/423 W |
| 4,697,808 | 10/1987 | Larson et al. .................... | 128/423 W |
| 4,711,242 | 12/1987 | Petrofsky et al. ............. | 128/423 W |
| 4,760,850 | 8/1988 | Phillips et al. .................. | 128/423 W |

OTHER PUBLICATIONS

"Experimental Correction of Footdrop by Electrical Stimulation of the Peronial Nerve" by Waters et al, J. of Bone & Joint Surg.; vol. 57A No. 8; Dec., 1975; pp. 1047-1054.
"Computer Synthesized Walking ... " by Petrofsky et al; J of Neuro. & Orth Med & Surg. vol. 6, No. 3 Oct. 1985 pp. 209, & 219-230.
"Computer Controlled Walking ... " by Petrofsky et al; J of Neuro. & Orth. Surg. vol. 4 No. 2 Jul. 1983 pp. 153-164.
Jun. 1969, J. Saltiel, *A One-Piece Laminated Knee Locking Short Leg Brace*, Orthotics & Prothetics, vol. 23:7, pp. 68-75.
Winter 83-84, E. Harrington et al., *Use of Anterior Floor Reaction Orthosis in Patients with Cerebral Palsy*, Orthotics & Prothetics, vol. 37:4, pp. 34-42.
1986, Yang et al., *Floor Reaction Orthosis: Clinical Experience*, Orthosis & Prothetics, vol. 40:1, pp. 33-37.

*Primary Examiner*—David M. Shay
*Attorney, Agent, or Firm*—Pennie & Edmonds

[57] ABSTRACT

A functional electrical stimulation orthosis for restoring locomotion in paraplegics is described. The orthosis has knee locks for each leg to enforce knee extension in a standing position, and a sensor located on each leg for sensing knee flexion. A plurality of electrodes are disposed on each leg to stimulate extension and flexion movements under the control of the patient. The orthosis can be used with crutches and stimulation of flexion and extension movement can be effected manually or automatically using an open-loop or closed-loop system. Various embodiments and modifications of the invention are disclosed. The orthosis can also be used in combination with other orthosis such as a foot ankle orthosis to provide a hybrid orthosis.

7 Claims, 1 Drawing Sheet

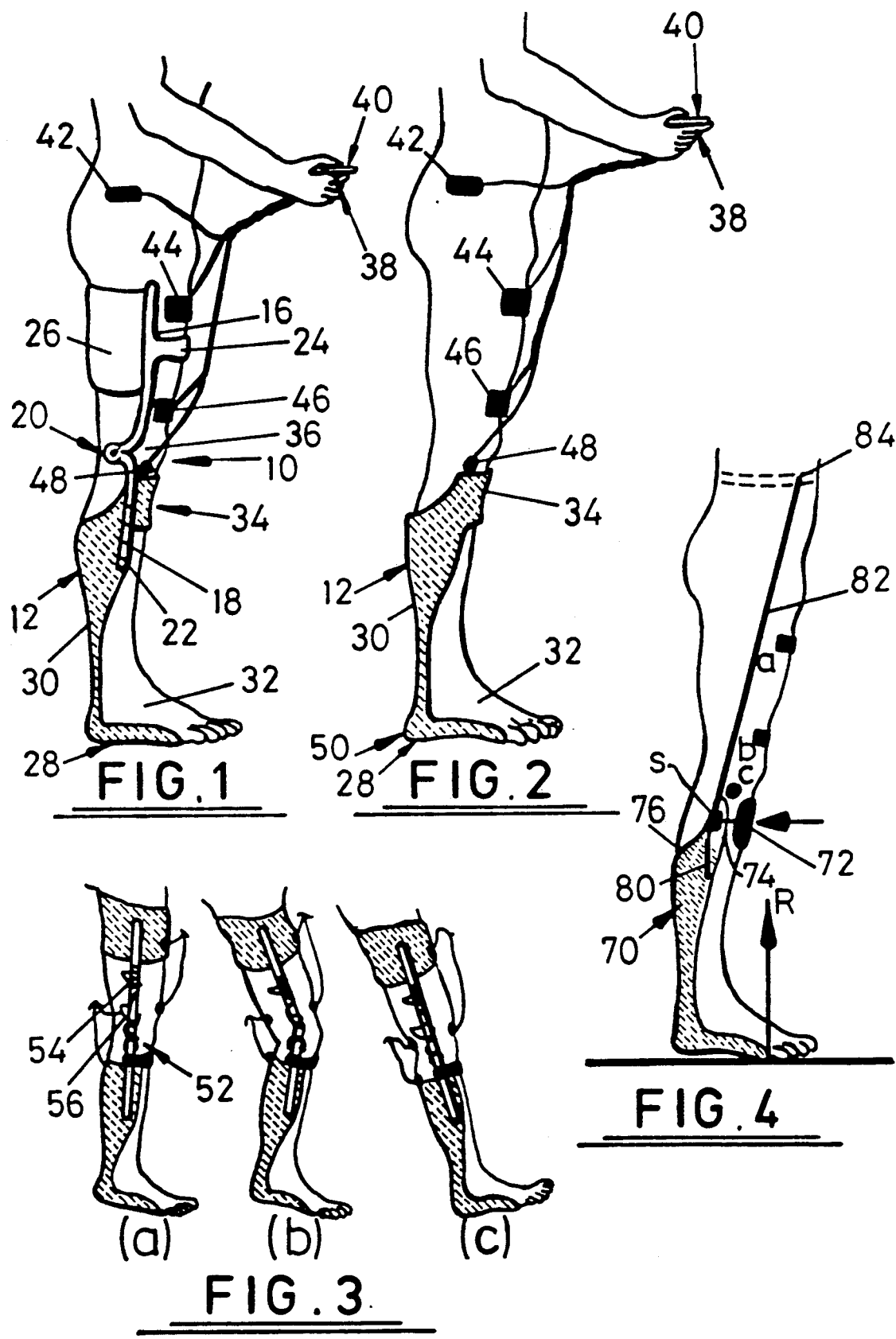

HYBRID ORTHOSIS

This is a continuation of application Ser. No. 928,061, filed Nov. 6, 1986, now abandoned.

The present invention relates to functional electric stimulation orthoses for restoring locomotion in neurologically impaired patients such as paraplegics.

Functional electrical stimulation (F.E.S.) orthoses are devices which include a mechanical structure which support paraplegic limbs, usually lower limbs, and a plurality of electrodes adapted to overlie muscles of the paraplegic limbs and which can be energised in a predetermined sequence to stimulate the muscles to cause certain movements of the limbs to provide a variety of functions, such as walking, standing or sitting. However, although there are many such devices most of them are impractical because they do not permit satisfactory simulation of the normal locomotion. Some existing orthoses permit a cumbersome waddling-type gait which is not only tiring for the paraplegic but the type of movement is unnatural and is difficult to control.

A functional electrical stimulation orthosis should satisfy a number of basic criteria in addition to being inexpensive, easy to manufacture and reliable. When used with paraplegics it should be capable of causing movement to resemble normal locomotion and to be used with or without walking aids depending on the degree of paraplegia. It should require minimal hardware and be relatively light-weight to minimise the impediments to paralegic gait. In addition, the orthosis should be completely controllable by the user and should permit a number of different movement activities such as standing up, walking on a flat surface, walking up and down stairs, standing up straight and sitting down from a standing up position. In addition, in the event of failure of the control system the mechanical components should be capable of providing mechanical stability for the paraplegic when in the standing position and use of the F.E.S. orthosis should avoid premature muscle fatigue.

An object of the present invention is to obviate or mitigate disadvantages associated with the aforementioned functional electrical stimulation orthosis.

Accordingly, in one aspect of the invention there is provided a functional electrical stimulation orthosis for restoring locomotion in paraplegic patients. The orthosis comprises knee locking means, sensor means, control means, and, first and second electrode means:

The knee locking means are adapted to be secured to each leg of a paraplegic patient for enforcing knee extension in a standing position.

The sensor means are located on each leg for sensing knee flexion of that respective leg.

The control means are coupled to each sensor means for receiving sensor signals produced therefrom in response to knee flexion, said control means having desired movement selector means actuable by the patient for providing output control signals for providing a desired movement by the patient.

The first electrode means are coupled to said sensor means and adapted to be associated with a knee extension reflex mechanism for providing electrical stimulii to said knee extension muscles in response to a first control signal from said control means.

The second electrode means are coupled to said sensor means and adapted to be associated with a knee flexion reflex mechanism for providing electrical stimulii to said knee flexion reflex mechanism in response to a second control signal from said control means.

The arrangement being such that, in use, when said desired movement selector means is actuated for a desired stance situation, knee extension and patient stability is maintained by said control means responding to knee flexion signals from each of said sensor means by providing said first control signal to said first electrodes to provide electrical stimulation of said knee extension reflex mechanism, and when said user selection control means are selected to provide desired locomotion, said knee extension control signal to one leg is disabled and said second control signal is provided to said second electrode means to electrically stimulate said knee flexion reflex of the same leg to permit the leg to swing forward and allow locomotion.

Preferably, the knee locking means consists of an ankle and calf support and a thigh support coupled together by hinge means, the thigh support being proportioned such that, in use, in the stance condition, the hinge means is disposed rearwardly of the natural knee joint so that the line of action due to body weight passes in front of the hinge means.

Preferably also, the sensor means is a microswitch associated with the hinge means, the microswitch being normally closed in full knee extension. Alternatively, the sensor means may be potentiometers or any suitable sensor responsive to angular displacement such as a goniometer.

In an alternative embodiment, the knee locking means is a resilient ankle and calf support with the line of action of the bodyweight vector, that is, the vertical line through the center of gravity of the body causing a resilient reaction force in the ankle and calf support to provide a knee locking force. Preferably also, the sensor means is a heel switch disposed in the base of the ankle and calf support and is responsive to heel lift as indicative of knee flexion to provide a sensor signal to said control means.

Alternatively, the sensor means in the alternative arrangement is a strain gauge for sensing strain in said ankle and calf support. Also, in the alternative embodiment a pressure sensor may be located under the ball of the foot to avoid potential instability just prior to the heel raised from the floor to permit the knee extensors and/or hip extensors which extend the knee joint, to be stimulated a predetermined time in advance of when they are normally stimulated.

Preferably, four electrodes are used to provide electrical stimulation of each leg and these are arranged in three pairs each requiring three control channels, the electrodes being located at, (a) the side of the gluteal muscles (medius and maximus) to give hip extension and pelvic stabilisation;

(b) upper anterior thigh for quadraceps stimulation;

(c) lower anterior thigh for quadraceps stimulation;

(d) over the anterior head of the fibula at the side of the peroneal nerve, electrodes (a) and (b) are used for gluteal stimulation, electrodes (b) and (c) are used for quadraceps stimulation and electrodes (c) and (d) are used for stimulation of the common peroneal nerve flexion withdrawal reflex. Preferably the electrodes are surface electrodes. Alternatively the electrodes are implantable electrodes.

Alternatively, the knee locking means may be provided by a brake or clutch mechanism, for example a solenoid and spring loaded bail lock or a magnetic particle brake or a mechanical clutch with Bowden cable from crutch hand grips. Preferably, the orthosis could be used with crutches and stimulation control means incorporated into the crutch hand grips.

Preferably said knee locking means includes position sensing means for determining the position of a floor reaction vector (FRV) line of action of a floor reaction force, and said position sensing means providing a signal to said first electrode means when said FRV passes within a certain distance of the knee joint axis. Preferably also said position sensing means consists of a patella pad coupled to the ankle and calf support by a strap, the tension in said pad being used to determined the position of the FRV. Conveniently said tension is sensed by displacement of a resilient spring loaded switch disposed in line with the pad and coupled to the ankle and calf support.

Preferably said resilient spring loaded switch has a compression spring and said spring tension is adjustable to set a threshold tension, so that an electrical signal is sent to said first electrode means, when a predetermined threshold is reached.

Conveniently the spring loaded switch is in series with the stimulation output to the quadraceps whereby stimulus to the quadraceps is automatically delivered to the quadraceps whenever the strap tension falls below the threshold.

In another aspect of the invention there is provided a floor reaction hybrid orthosis comprising, a floor-reaction foot-ankle orthosis, and an FES control system, said FES control system including first electrode means adapted to be disposed on said quadraceps for stimulation thereof to provide knee extension, and second electrode means adapted to be disposed in proximity to an afferent nerve for activating said knee tension, floor reaction vector (FRV) position sensing means for sensing the position of said floor reaction vector and stimulating said quadraceps via said first electrode means when said FRV passes within a predetermined distance of said knee joint axis.

This is achieved by using a patella pad and resilient spring loaded strap coupled between the pad and the orthosis. The arrangement being such that when the strap tension exceeds a preset threshold, indicative that the FRV is approaching the knee axis, the switch trips and a signal is sent to said first electrode means to stimulate the quadraceps.

Embodiments of the present invention will now be described by way of example, with reference to the accompanying drawings in which:

FIG. 1 is a diagrammatic side elevation of a right leg carrying a first embodiment of an F.E.S. orthosis according to the invention;

FIG. 2 is a view similar to FIG. 1 of a second embodiment according to the invention;

FIG. 3a is an upright stance, FIG. 3b is a knee flex, and FIG. 3c is a heel strike diagramatic side elevation of the orthosis shown in FIG. 1 with a different knee locking mechanism;

FIG. 4 depicts a hybrid orthosis for use in assisting prolonged standing and walking in neurologically impaired patients.

Reference is first made to FIG. 1 of the drawings which illustrates a first embodiment of functional electrical stimulation orthosis. It will be understood that although only one leg is shown the part to be described and which are illustrated are also applied to the left leg. The F.E.S. orthosis comprising a leg support brace generally indicated by reference numeral 10 which consists of a lower moulded plastic resilient calf and ankle support 12 and an upper rigid metallic thigh support generally indicated by reference numeral 14. The upper thigh support consists of a first upwardly extending elongate portion 16 and a lower downwardly extending elongate portion 18 which is joined to the portion 16 by a hinge 20. The lower portion 18 is fastened to the orthosis 12 by means of screws (not shown) which are received by drilled holes 22 in the portion 18. The upper portion 16 has an integral anteriorally extending thigh support bar 24 which joins with a like upper thigh support on the inside of the leg (not shown). A posterior thigh support 26 made from fabric is also attached to upper portion 16 for relieving pressure during movement and is one of the areas designed to give three point support. The fabric support deforms during sitting to avoid potential pressure sores or tissue damage problems.

The ankle and calf support 12 consists of a foot support portion 28 which is integral with a calf support portion 30 and which prevents the calf support portion from slipping up and down the leg during locomotion. The support is flexible around the ankle joint 32 and does not significantly impede movement by the paraplegic. The orthosis has an integral knee band generally indicated by reference numeral 34 which extends across the anterior portion of the leg just below the knee at the level at the top of the fibula and tibia. Because support 12 is resilient the weight of the paraplegic pushes against the knee band causing a reaction force due to resilience of the knee band which tends to lock the knee and stabilise the paraplegic when standing.

It will be seen that the joints 20 are offset rearwardly from the upper and lower elongate portions and behind the natural knee joint axis. The line of action of body weight passes in front of the hinge joints 20 for standing so that throughout most of the stance phase this joint will maintain the natural knee joint and stable knee extension. The hinge joint also incorporates a microswitch sensor or any other suitable sensor such as a rotary potentiometer, to detect when the joint 20 is fully extended or flexed and this sensor is used by the control system as will be later described to control the application of stimulii to the muscles of the paraplegic to provide muscle stimulation for a desired movement.

A hand held control unit 38 has a plurality of selector switches 40 located thereupon for actuation by the user to form a desired movement. It will be appreciated that although this is shown as a hand held unit it could readily by incorporated into the arm of a crutch.

The control unit is connected via conductors to a plurality of electrodes located at the strategic positions over the paraplegic's limb to permit stimulation of extensor and flexor reflex mechanisms to cause a variety of movements to occur. Four electrodes are shown in this embodiment and these are sufficient to permit a variety of different movements to be obtained. A gluteal electrode 42 is located over the gluteal medius and maximus muscles so that when stimulated gives hip extension and pelvic stabilisation. An upper thigh electrode 44 is located over the anterior portion of the thigh and when energised stimulates the upper quadraceps and also doubles for gluteal stimulus with electrode 42, as will be explained. A lower quadraceps electrode 46 stimulates the lower quadraceps when energised and also functions with peroneal electrode 48 for stimulation of the peroneal nerve to actuate the flexion withdrawal mechanism as will also be explained.

Electrode pairs, 42 and 44, 44 and 46, and 46 and 48, may be stimulated through a respective single channel thus requiring three channel stimulation controlled by the control unit. This will be best explained by reference to the different locomotion functions and movement requirements to be carried out by the paraplegic.

It will be understood that the individual channels of the stimulator are known per se and that the nature and magnitude of the signals required to stimulate the individual muscles and nerves mentioned are also known as are the type of electrodes and electrode material.

Operation of the apparatus of FIG. 1 may be best explained by reference to different desired movement situations which illicit different control signals and logic from the control unit 38.

Firstly, movement of the paraplegic from a sitting to a standing position, this will now be described. In the sitting position no stimulation is applied and the knees are flexed. When the paraplegic wishes to stand he first moves to the edge of the seat and positions his feet appropriately on the floor. He then presses a control switch marked "STAND" and, after a delay of approximately four seconds to permit the paraplegic to adjust his forward leaning posture and to hold on to supports if necessary, for example if he is sitting in a wheelchair, stimulii is then applied to the knee extensor muscles, i.e. the quadraceps, via electrodes 44 and 46. Because of the configuration of his body contraction of the quadraceps cause him to be raised to the standing position as shown in FIG. 1. The paraplegic can assist in this movement by taking part of his body weight on his arms if there are arm rests available.

In the standing position as shown in FIG. 1, the knee joints are in full extension as sensed by the microswitches in the joints 20 and the stimulus is removed shortly afterwards. Stability is maintained in the upright standing position due to two factors. The first factor is by the mechanical force exerted by the resilient knee band of the calf and ankle support 12 and the second factor is the nature of the offset hinge 20 which lies behind the line of action of the body weight so that inadvertent flexion of the knee does not result in collapse of the paraplegic. Therefore, during standing no stimulus is required. However, should the knee inadvertently flex so that the microswitch 36 is opened this is sensed by the control unit 38 which in turn sends a signal to electrodes 44 and 46 to electrically stimulate and extend the quadraceps and cause the knee to extend until the microswitch 36 closes and registers the knee joints as being fully extended. In this way the reflex loop is maintained and stability is automatically maintained.

Sitting is the reverse process and in this case when the paraplegic desires to sit he presses the "SIT" switch and electrical stimulii is then applied to the quadraceps for slowly decreasing amplitude via electrodes 44 and 46. The paraplegic responds to this stimulus by leaning backwards and flexing his knees and slowly returns to his seat. The slowly decreasing stimulii to the quadraceps causes some contraction of the quadraceps sufficient to compensate for the body weight during sitting so that the paraplegic does not simply collapse in the seat but rather slowly returns to the seat. The automatic action of the quadraceps coming on in response to the knee opening may be thought of as an artificial reflex which stimulates the normal reflex mechanism.

During walking the paraplegic may use crutches and, in this case, the control system uses two additional hand controls, one mounted on each crutch handle. Crutches are not shown in the interests of clarity. Also, two additional channels of stimulii are used per leg. In order for the subject to make a step forward the paraplegic firstly transfers his body weight to the stance limb and the stance limb stability is maintained by the offset knee joint and, should the need arise, by the automatic knee extension reflex. The subject then presses a switch on the control unit which inhibits the automatic knee extension reflex of the other leg and stimulii is simultaneously applied to the peroneal nerve via the peroneal nerve electrode 48 on the swing leg which illicits the flexion withdrawal reflex causing simultaneous reflexion at the hip, knee and ankle and to the gluteal muscles of the stance limb to stabilise the pelvis. However, it should be noted that pelvic stability can be obtained in some paraplegics without the requirement of gluteal stimulus by the paraplegic using the latissimus dorsi and trapezius muscles and applying stabilising force actions through the crutches. The use of gluteal stimulus, however, reduces the effort required of the upper limb. The gluteal muscles of the swing limb may also be stimulated using electrodes 42 and 44 to provide abducting action which is sometimes necessary in paraplegics with adductor spasticity to ensure the correct positioning of the foot at the end of the swing phase. This may also be dealt with by using a mechanical linkage between the legs that prevents them from coming too close together whilst not restricting the other required motions.

During walking, when the paraplegic removes his finger from the knee extension inhibit control switch the knee extension reflex enables the control unit 38 to send stimulii to the knee extensors through electrodes 44 and 46 causing the knee to extend just before heel strike. The gluteal stimulus is maintained until shortly after heel strike whereupon the paraplegic transfers body weight to the stance limb and the cycle repeats. The left and right leg alternate the role of stance limb to give a reciprocal gait pattern.

It will be appreciated that stair or step climbing activity using the orthosis with crutches may be possible and in this case body weight is transferred by the paraplegic to his stance limb and the other leg is flexed to land the foot on the next step and then apply knee extension and shifting the body weight to the stance leg for flexing the other leg to lift it on to the same step or the next step. The orthosis can have a leg brace on one side of the leg only.

Reference is now made to FIG. 2 of the drawings which is substantially the same as FIG. 1 except that the upper thigh support 14 is not used. In this case only the lower ankle support 12 is used and the same electrodes 42 and 44, 46 and 48 are also used in identical positions to that shown in FIG. 1. However, the ankle and calf support 12 incorporate a heel switch generally indicated by reference numeral 50 in the base of the support. The presence of the heel switch enables the knee extension reflex to be implemented because if the heel is raised from the ground the switch opens and sends a signal to the control unit 38 which causes electrical signals to be sent to electrodes 44 and 46 to stimulate the quadraceps to extend the knee so that the heel returns to the ground. It will be appreciated that the ankle and calf support 12 is sufficiently rigid and resilient so that when the subject is upright and the knee flexes, the heel must rise with the foot pivoting about the toes and that the resilience is such that the band 34 assists in "locking" the knee in the extended position.

As with the first embodiment described with reference to FIG. 1, the electrode pairs for gluteal, quadraceps and peroneal stimulation are the same and similarly the paraplegic can also achieve pelvic stabilisation using the latissimus dorsi and trapezius muscles together with force actions transmitted through crutches. It will be appreciated that an advantage of the function of electrical stimulation is that paraplegic effort is considerably reduced. It will also be appreciated that the stimulus to the quadraceps stops shortly after the heel switch registers that the stability has been restored to avoid undue muscle fatigue.

Reference is now made to FIG. 4 of the drawings which depicts a hybrid orthosis consisting of floor reaction AFO 70, knee extensor electrodes (a) and (b), knee flexion electrode (c) and a patella pad 72 coupled via a strap 74 to a resiliently biased switch (5) mounted on the upright portion 76 of the AFO 70.

Electrode (b) was common to both channels acting as an indifferent electrode. Monophasic, rectangular pulses were used having a duration of 0.3 ms a pulse repetition frequency of 20 Hz and an amplitude adjustable up to 120 volts (measured with a 1kohm load). Stimulation of the knee extensors electrodes was delivered through two 41 mm × 88 mm self adhesive electrodes (Myocare type 6282 m 3M Ltd.), labelled (a) and (b) in FIG. 4. When stimulating the common peroneal nerve a smaller active electrode was positioned just behind the head of fibula as shown in FIG. 4.

A semi-automatic, standing posture, stabilising control loop has been incorporated to avoid fatiguing the quadriceps. During reciprocal walking the FES system delivered appropriately patterned stimuli to the quadriceps muscles and the common peroneal nerve. The latter was used to elicit a flexion withdrawal reflex to initiate the swing phase of gait.

Standing up from a seated position was assisted by open-loop stimulation of the quadriceps in a manner similar to that described above. Once upright, the subject leans forward slightly so that the foot/floor reaction vector (FRV) passes the knee joint axis anteriorly as shown. In this case a moment is generated at the ankle joint by the floor reaction force (R). This moment is opposed by a force (F) due to the pressure applied by the patella pad 72. In this posture the AFO 70 stabilises the leg without the need for continued stimulation of quadriceps. However, should the direction of the FRV pass behind the knee joint axis the leg will destabilise. The position of the FRV relative to the knee joint axis can be sensed by measuring the tension generated in the patella pad restraining strap 74. The strap tension was used to control the application of quadriceps stimulation. When the strap tension fell below a preset level, indicating that the direction of the FRV was too close to the knee axis, the quadriceps were maximally stimulated until the strap tension again exceeds the preset level. This requires the subject to be aware of the stimulation and to make the required postural shift by leaning forwards. Subjects who have used this orthosis have had preserved sufficient sensation to be aware of the applied stimulus. Feedback may alternatively have been provided by stimulating a sensitive area of skin or by using some audio visual cue. In the HO the strap tension was sensed by the small displacements of a compression spring (not shown) mounted in line with the strap and affixed to the plastic AFO upright 76. The threshold tension was set by adjusting the displacement required to turn off the electrical switch(s). This switch was in series circuit with the stimulator output to quadriceps. In this way stimulus was automatically delivered to the quadriceps whenever the strap tension falls below threshold.

It has been previously determined that a minimum of four channels of electrical stimulus are required to synthesise a simple reciprocal gait pattern in paraplegics, KRALJ A., BAJD T., TURK R., KRAJNIK J. AND BENKO H. (1983). Gait restoration in paraplegic patients. A feasibility demonstration using multichannel surface electrode FES. J. Rehabil. R&D, 20, No. 1 (BPR10-38), p 3-20. During the stance phase, the knee extensor muscles were activated and the swing phase was accomplished by eliciting the flexion withdrawal reflex by stimulating an afferent nerve. A similar approach was used for the HO described here.

From the patient's control point of view, the gait cycle was divided into stance and swing phases. For each leg the transition from one phase into another was achieved by pressing a corresponding hand switch. These hand switches were mounted onto the handgrips of the forearm crutches or walking frame/rollator. When a switch was not pressed the stance phase control loop described above was enabled. In order to take a step forward, the subject first transfers his body weight onto the contralaterial supporting leg and presses the ipsilateral hand switch. Whilst the switch was pressed ipsilateral stimulation of quadriceps was disabled and the common peroneal nerve stimulated. Stimulation of this mixed nerve elicits a flexion withdrawl response producing dorsiflexion and eversion of the foot and flexion of the hip and knee. The amount of flexion was dependent upon the preset stimulus intensity. To terminate the swing phase prior to foot contact, the hand switch was released and the automatic control of quadriceps re-enabled. This resulted in the immediate stimulation of quadriceps, causing the knee to extend at foot contact. The quadriceps stimulus was maintained until mid stance when the patella strap tension again exceeded the threshold. The duration of the swing phase was regulated by the time of pressing the switch. Flexion may, optionally, by triggered using a conductive rubber insole switch, with the active element positioned in the region of the metatarsal joints. When the subject transfers his body weight onto the stance limb this action unloads the switch causing it to change state. This change of state causes the quadriceps stimulus to be inhibited and the peroneal stimulus to be applied for a preset time interval. This preset interval was adjusted to suit the subjects preferred cadence. In order to prevent false triggering of flexion it was necessary to build in the condition that the metatarsal switch be unloaded for an uninterrupted period of 0.1s before allowing flexion.

Two patients with spinal cord lesions have so far been included in the trials of the HO. In both cases quadriceps restrengthening exercises were undertaken using cyclical stimulation in a manner similar described to that described above.

The first subject (K.D, male age 34 yrs, mass 88 kg, height 1.88 m, lesion T5/6 complete, 4 yrs post injury) used the HO bilaterally using the handgrip mounted switches to control flexion when walking with a rollator type walking aid. The second subject (G.D, male aged 22 yrs, mass 70 kg, height 1.8 m, incompletely lesioned at the level C6, 3 yrs post injury) had one leg that was completely paralysed whilst the other had sufficient voluntary control to enable him to remain standing for a short time using forearm crutches without stimulation. He had previously used a 2 channel FES device described in BAJD T., ANDREWS B.J., KRALJ A., KATAKIS J. (1985). Restoration of walking in patients with incomplete spinal cord injuries by use of surface electrical stimulation. Prosthetics and Orthotics International, vol 9, No. 2, pp 109-111. This subject used the HO unilaterally for standing and walking in forearm crutches fitted with handgrip switches for flexion control. This patient preferred the option of automatic triggering of flexion for level ground walking. He used manual control, as he did with his 2 channel FES device when negotiating uneven ground and steps.

The preliminary trials indicate that the HO was effective in stabilising the knee joint when applied unilaterally or bilaterally. Stimulation of the quadriceps was significantly reduced prolonging standing times almost indefinitely. The wearing of an AFO is cosmetically acceptable and does not interfere with level ground walking. The FES assisted walking may require less energy than walking in knee ankle foot braces with locked knee because no hip hiking is necessary with active flexion. Finally, FES-assisted walking is more aesthetic than locking knee gait for the observer and is prefered by the patients. There may be a number of therapeutic benefits to be gained from the use of FES based orthosis. These may include prevention of pressure sores, contractures, muscle atrophy and bone demineralisation.

It will be appreciated that various modifications may be made to the embodiments hereinbefore described without departing from the scope of the invention.

For example, with regard to the embodiment described with reference to FIG. 1, it will be understood that a different upper thigh support could be used to provide the knee locking mechanism and knee stability when in a stance position. This could be provided by the arrangements as shown in FIGS. 3a, 3b and 3c in which a solenoid actuated mechanism 52 is provided for knee locking. It will be seen that in FIG. 3a which is the upright stance position, the knee mechanism 52 is locked and in order to walk a signal is sent to a solenoid 54 which retracts a lever 56 which rotates a link out of a locking position permitting the knee to flex as shown in FIG. 3b. At toe off and during the swing phase to the position as shown in FIG. 3c, which is heel strike, the knee reflex mechanism is initiated because of the signal from the knee mechanism indicating flexion causing the quadriceps to extend the knee at heel strike. It will be appreciated that other actuators may be used instead of the solenoid such as magnetic particle brakes or a mechanical clutch with Bowden cable from the crutch handgrips. It will also be understood that stimulus can be applied through surface, percataneous or implanted electrodes.

In addition, with regard to the embodiment shown in FIG. 2, it will be understood that means for detecting flexion could be provided other than by the heel switch 50, for example, a strain gauge could be located in the region of the ankle to detect strain in the ankle and calf support 12 and this signal used to initiate the knee extensor reflex mechanism to maintain stance stability. Also, a pressure sensor could be located under the ball of the foot at the toes to protect potential instability just prior to the heel being raised from the floor and this could be used to provide a signal to the control unit which would permit the quadriceps to stimulated about 200 milliseconds earlier than normal to improve stance stability.

In the hybrid orthosis (HO) shown in FIG. 4, the strap and/or the compression spring may be replaced by an elastomeric variable resistance transducer for example a Flexigauge (trademark), Flexigage Ltd., Glasgow, Scotland which can be used to sense strap tension, and a comparator can be used to deliver automatically a stimulus whenever the strap tension falls below the threshold.

It will also be understood that the materials and components used herein are exemplary only and may be replaced by other like materials and components to provide a similar function. For example, the thigh support may be plastic.

It will be appreciated that the crutch handle mounted hand controls may be simple switches or devices giving a degree of proportional control, for example, a pressure transducer such that the harder it is pressed the greater the intensity of stimuli to the peroneal nerve and the greater the limb flexion reflex. This is useful in adjusting the stepping height to accommodate changes in terrain or obstacles and also it will be appreciated that the joint microswitches could equally be potentiometers in which case proportional closed-loop control could be implemented.

In the embodiments hereinbefore described the system is open-loop insofar there is no feedback from the flexion reflex to terminate the flexion reflex and stimulate the extension reflex. Termination is carried out by the patient using the hand switch. In a closed loop system flexion is initiated by unloading the leg as sensed by a pressure switch under the metatasals of each foot. Stimulus is then transmitted to the flexion electrodes as described above to cause hip and knee flexion. The stimulation is terminated when a particular hip angle is reached as sensed by using hip goniometers thus the system is closed-loop and operates automatically. The closed-loop system compensates for differences between patients and optimises stimulation and gait for each particular patient and avoids response fatigue. The hip goniometer may conveniently be in the form of a displacement potentiometer 80 mounted on the shank and inextensible flexible cord 82 connecting the displacement potentiometer to the patients waist (e.g. belt) 84 as seen in FIG. 4. This is also applicable to the embodiment shown in FIGS. 1 to 3.

Also the hip abductors and flexors on the contralateral side may be stimulated during single support to stabilise the pelvis. A safety feature is that if the hip angle is not reached in a predetermined time the stimulus is removed and this is readily achieved using a comparator circuit.

Advantages of the embodiments of the apparatus are that they are inexpensive, simple to construct and install and offer minimal impedement to paraplegics during a variety of locomotion activities. In addition, the muscles are used only for short duration and antigravity support during standing is provided by the mechanics thus reducing the time before the onset of muscle fatigue. The mechanical arrangement in FIG. 1 provides a fail safe mechanism in the event of electrical disconnection or muscle fatigue because the offset hinges are behind the line of action of body weight thus providing inherent stability in the standing position. A further advantage is that the orthosis ccan be used for the paraplegic to move between an upright and sitting position without the need for other pieces of apparatus although it will be appreciated that use of such apparatus, such as crutches, may be of assistance.

The orthosis can also be used to train the posture of paraplegics. For example, a visual indication of stimulation to occur is given to the paraplegic who can then orient this body to facilitate movement by the F.E.S. when stimulation does occur.

I claim:

1. A floor reaction hybrid orthosis for assisting locomotion in neurologically impaired patients, said orthosis comprising:

a floor reaction foot ankle orthosis located on each paralysed leg of a patient for enforcing knee extension;

sensing means coupled to each leg for sensing a resultant knee extending force acting on a respective paralysed leg by a floor reaction force acting through each respective floor reaction orthosis in the weight bearing condition;

stimulation means for providing a free knee during walking and necessary knee-locking only by stimulating the leg muscle, said stimulation means coupled to said sensing means and being arranged so that when the respective resultant knee extending force is sensed to be inadequate to extend the respective knee, said stimulation means stimulates leg extension muscles of at least that leg to stabilize the leg in the extended positions without a separate mechanical knee lock and when the resultant knee extending force is sensed as being adequate due to the patient restoring posture, said stimulation is removed, thereby providing a free knee during walking and necessary knee-locking by stimulating the leg muscle in response to the resultant knee extending force as sensed.

2. A hybrid orthosis as claimed in claim 1 wherein said floor reaction orthosis is formed by an ankle-foot orthosis.

3. A floor reaction hybrid orthosis as claimed in claim 1 wherein said sensing means is disposed on the patient's leg approximately at the knee.

4. A floor reaction hybrid orthosis consisting essentially of:

a floor reaction foot-ankle orthosis; and an FES control system, said FES control system including first electrode means adapted to be disposed on a patient's quadriceps for stimulation thereof to provide knee extension, second electrode means adapted to be disposed in proximity to an efferent nerve for activating knee flexion, and floor reaction vector (FRV) position sensing means for sensing the position of a floor reaction vector and stimulating said quadriceps via said first electrode means when said FRV passes within a predetermined distance of the patient's knee joint axis.

5. A hybrid orthosis as claimed in claim 4 wherein said FRV sensing means includes a patella pad coupled by a strap to a resiliently biased switch mounted on the orthosis, the arrangement being such that when the strap tension exceeds a preset threshold, indicative that the FRV is approaching the predetermined distance from the knee joint axis, the switch is tripped and a signal is sent to said first electrode means to stimulate the quadriceps.

6. A method of controlling stance in a patient using a floor reaction hybrid orthosis comprising the steps of:

providing a floor reaction orthosis to support a or each leg of a patient to maintain the patient in a stance condition, with a free knee during walking;

sensing a resultant knee extending force relative to the or each knee joint of each leg;

stimulating leg extension muscles of the respective leg when the resultant knee extending force is sensed to be inadequate to extend the leg;

locking the patient's respective knee only by said stimulation; and removing the stimulation once the posture of the patient is corrected and the resultant knee extending force is adequate to extend the leg.

7. A method as claimed in claim 6 wherein the step of sensing includes sensing the resultant knee extending force due to the force acting through the floor reaction orthosis at the knee joint.

* * * * *